United States Patent
Villamil Torres et al.

(10) Patent No.: US 9,987,239 B1
(45) Date of Patent: Jun. 5, 2018

(54) PHARMACEUTICAL RETINOID PREPARATION FOR TOPICAL USE

(71) Applicants: Julio César Villamil Torres, Bogota (CO); Camilo Rey Ferro, Sunrise, FL (US)

(72) Inventors: Julio César Villamil Torres, Bogota (CO); Camilo Rey Ferro, Sunrise, FL (US)

(73) Assignee: Rey Ventures, LLC, Sunrise, FL (US)

( * ) Notice: Subject to any disclaimer, the term of this patent is extended or adjusted under 35 U.S.C. 154(b) by 0 days. days.

(21) Appl. No.: 15/458,071

(22) Filed: Mar. 14, 2017

(51) Int. Cl.
| | |
|---|---|
| A61K 31/192 | (2006.01) |
| A61K 9/00 | (2006.01) |
| A61K 9/06 | (2006.01) |
| A61K 9/107 | (2006.01) |
| A61K 47/32 | (2006.01) |
| A61K 47/12 | (2006.01) |
| A61K 47/34 | (2017.01) |
| A61K 47/10 | (2017.01) |
| A61K 47/18 | (2017.01) |

(52) U.S. Cl.
CPC .......... *A61K 31/192* (2013.01); *A61K 9/0014* (2013.01); *A61K 9/06* (2013.01); *A61K 9/107* (2013.01); *A61K 47/10* (2013.01); *A61K 47/12* (2013.01); *A61K 47/18* (2013.01); *A61K 47/183* (2013.01); *A61K 47/32* (2013.01); *A61K 47/34* (2013.01)

(58) Field of Classification Search
CPC ...... A61K 31/192; A61K 9/0014; A61K 9/06; A61K 9/107; A61K 47/32; A61K 47/12; A61K 47/34
See application file for complete search history.

(56) References Cited

U.S. PATENT DOCUMENTS

| | | |
|---|---|---|
| 4,717,720 A | 1/1988 | Shroot et al. |
| 5,212,303 A | 5/1993 | Shroot et al. |
| 7,579,377 B2 | 8/2009 | Graeber et al. |
| 7,737,181 B2 | 6/2010 | Graeber et al. |
| 7,834,060 B2 | 11/2010 | Graeber et al. |
| 7,838,558 B2 | 11/2010 | Graeber et al. |
| 7,868,044 B2 | 1/2011 | Graeber et al. |
| 7,998,467 B2 | 8/2011 | Mallard et al. |
| 8,404,220 B2 | 3/2013 | Ebel et al. |
| 8,653,140 B2 | 2/2014 | Graeber et al. |
| 8,703,820 B2 | 4/2014 | Graeber et al. |
| 8,716,341 B2 | 5/2014 | Doutremepuich |
| 8,729,127 B2 | 5/2014 | Graeber et al. |
| 8,921,423 B2 | 12/2014 | Graeber et al. |
| 2009/0318371 A1 | 12/2009 | Ayala |
| 2013/0338230 A1 | 12/2013 | At |
| 2017/0014398 A1* | 1/2017 | Kandavilli ......... A61K 31/7004 |

FOREIGN PATENT DOCUMENTS

WO    WO 2016033308    *  3/2016

* cited by examiner

*Primary Examiner* — Shirley V Gembeh
(74) *Attorney, Agent, or Firm* — The Morales Law Firm, LLC; Joseph L. Morales (57) ABSTRACT

The present invention relates to compositions and manufacturing methods of topical adapalene preparations, which include a solvent-lipid complex in order to keep the active pharmaceutical ingredient dissolved in a vehicle whose external or continuous phase is aqueous. Thus, a pleasant non-oily sensation is achieved at the moment of application, while greater retention of the active pharmaceutical ingredient is reached in targeted skin layers, thereby reducing systemic uptake in the blood.

16 Claims, 5 Drawing Sheets

PHARMACEUTICAL RETINOID PREPARATION FOR TOPICAL USE

FIELD OF THE INVENTION

The present invention relates to compositions and manufacturing methods of topical retinoid preparations, preferably topical adapalene preparations. More particularly, the present invention is related to retinoid formulations, preferably adapalene formulations, including a solvent-lipid complex that keeps the active pharmaceutical ingredient dissolved in a vehicle whose external or continuous phase is aqueous. Thus, a pleasant non-oily sensation is achieved when applied to the skin, while a greater retention of the active pharmaceutical ingredient is reached in targeted skin layers, thereby reducing systemic uptake in the blood.

BACKGROUND OF THE INVENTION

Chemically, adapalene is 6-[3-(1-adamantyl)-4-methoxyphenyl] naphthalene-2-carboxylic and belongs to the chemical group known as retinoids. Retinoids are chemical compounds structurally related to vitamin A. Their influence over epithelial cell growth has been exploited in a variety of medical contexts, especially in the area of treating skin conditions, particularly acne. Retinoids include first generation compounds such as retinol, tretinoin and isotretinoin; second generation compounds such as etretinate and acitretin; and third generation compounds such as tazarotene and adapalene. All retinoids are amphipathic, containing a cyclic end group, a polyene side chain and a polar end group.

While useful for treatment of skin conditions, adapalene can also cause undesirable side effects, especially with prolonged high exposure. Much of such toxicity is associated with blood uptake and resulting non-local effects that occur outside the area of topical administration.

Due to their chemical structure, retinoids have a very low water solubility. Particularly, the solubility of adapalene is $4 \times 10^{-6}$ mg/mL. This characteristic makes their incorporation into topical pharmaceutical preparations extremely challenging. In the current state of the art, two different approaches have been used to address this challenge: the first one is the dispersion of adapalene in finely divided or micronized particles, within a pharmaceutically acceptable base such as cream, gel, lotion, or ointment; the second one is the solubilización of adapalene in bases formed by non-aqueous excipients.

Whatever the approach used in the current state of the art, it has limitations which do not allow the maximum benefit that the topical use of adapalene can provide. First, according to the essential principles governing the penetration of substances through the skin, the initial step of the transport process consists in the dissolution of the molecules in a vehicle. Next, molecules partition into lipids of the stratum corneum, this means that the molecules pass from the hydrophilic environment composed of the vehicle to the lipophilic environment composed of the lipids that make up the outer layer of the stratum corneum. The molecules of active ingredients must then diffuse through the stratum corneum and reach the epidermis where inverse partition into the hydrophilic environment takes place. Inverse partition means that the molecules go from the lipophilic environment in which they were dissolved within the stratum corneum, to the hydrophilic environment of the viable epidermis.

When adapalene is dispersed as fine particles in an aqueous vehicle, its penetration is highly limited to the fraction that could be dissolved at the interface formed by the vehicle and stratum corneum of the skin, thereby limiting the amount and speed with which the active pharmaceutical ingredient penetrates and becomes available in the epidermis, where it should exert its pharmacological action.

On the contrary, if the approach to be used is to dissolve the adapalene in vehicles formed by non-aqueous solvents, the limitation is the fat or oily sensation created by this type of vehicles when the product is applied to the skin, leading to poor product acceptance by the patient, especially when considering that acne is the condition where adapalene is more often used. U.S. Pat. No. 7,579,377, U.S. Pat. No. 7,737,181, U.S. Pat. No. 7,834,060, U.S. Pat. No. 7,838,558, U.S. Pat. No. 7,868,044, U.S. Pat. No. 8,653,140, U.S. Pat. No. 8,703,820, U.S. Pat. No. 8,729,127, and U.S. Pat. No. 8,921,423 describe pharmaceutical compositions containing adapalene at a concentration of 0.3% by weight, which is suspended, undissolved, in a gel, cream, or lotion vehicle.

U.S. Pat. No. 8,716,341 describes pharmaceutical compositions containing adapalene from 0.02% to 0.04% by weight, which is suspended, undissolved, in a gel, cream, or lotion vehicle.

U.S. patent application US20090318371 (the "e'371 application") describes a combination of adapalene or tazarotene with clindamycin phosphate and benzoyl peroxide. This application does not specify whether adapalene is dissolved or suspended into the vehicle; however, from the described formulation, it is easily deductible that adapalene is not dissolved, since the solvent and quantities used for this purpose are not enough to get a true solution. The selected solvent is ethyl alcohol in a percentage of up to 10% of the total composition. In the best-case scenario covered by this application, adapalene 50 mg should be dissolved in a maximum of 10 g, equivalent to 12.7 mL, of ethyl alcohol. The concentration of adapalene in that composition is 50 mg/12.7 mL or 3.94 mg/mL. The solubility of adapalene in ethyl alcohol is 1 mg/mL. Thus, the mixture in the '371 application, with a concentration of 3.94 mg/mL, would not result in full dilution of adapalene.

U.S. Pat. No. 7,998,467 describes pharmaceutical compositions containing topical adapalene dispersed in polyurethane polymers in order to improve its absorption. As in the aforementioned documents, adapalene is not soluble in the preparation.

U.S. Pat. No. 8,404,220 describes a manufacturing process, at industrial scale, of adapalene aqueous gels, in which the active pharmaceutical ingredient is dispersed, undissolved, within a gel.

Japanese patent applications JP2008273941, JP2008255017, and JP2008184446, like the Chinese patent CN103462882, and patent application CN1989956 describe pharmaceutical preparations of adapalene, alone or in combination with other active pharmaceutical ingredients, in which it is explicitly stated that adapalene is suspended, undissolved, in the vehicle.

U.S. Pat. No. 5,212,303 describes both pharmaceutical preparations where adapalene is suspended, undissolved, in aqueous vehicles, and pharmaceutical preparations where adapalene is dissolved in a non-aqueous mixture of polyethylene glycol 400 and ethyl alcohol in a ratio of 70:30. The vehicle without water, which also has a 70% of polyethylene glycol, creates an oily sensation causing rejection by the patient, especially when considering that acne is the condition where adapalene is more often used.

SUMMARY OF THE INVENTION

It is one object of the present invention to provide topical composition, comprising water; adapalene at a concentration in a range of about 0.05% to 0.1%; and a complex consisting of a solvent and a lipid, which completely dissolves the adapalene and has a partition coefficient value for adapalene in water of 0.95 to 1. In a further embodiment, the solvent is present at a concentration in a range of about 1.0% to 15%. In a further embodiment, the lipid is present at a concentration in a range of about 0.5% to 10%. In another embodiment, the solvent is selected from the group consisting of N-methyl-2-pyrrolidone, diethylene glycol monoethyl ether, 2-pyrrolidone, glycofurol, dimethylsulfoxide, or mixtures thereof.

In another object of the present invention, the lipid is selected from the group consisting of oleic acid, stearic acid, linoleic acid, ethyl linoleate, methyl linoleate, or mixtures thereof. In a further embodiment, the composition contains one or more surfactants, one or more antioxidants, one or more chelating agents, one or more preservatives, one or more humectants, one or more gelling agents, and one or more pH modifiers. In another embodiment, the external or continuous phase is hydrophilic and the internal or discontinuous phase is lipophilic. In a further object of the invention, the composition, when tested under de microscope, does not show crystals of the active pharmaceutical ingredient. In further object of the present invention, a method for preparing the topical composition is provided, which comprises the following steps. A first step of combining ceteareth-12, oleic acid and PEG-12 glyceryl distearate are combined and warming the mixture to 45° C. to 65° C., preferably 55° C., under constant stirring, until obtaining a first homogeneous mixture; dissolving butylhydroxytoluene into the first homogeneous mixture. An additional step of dissolving disodium edetate, benzyl alcohol and poloxamer in a second vessel, in a fraction of water resulting in a second homogeneous mixture, and subsequently warming the second homogeneous mixture to 45° C. to 65° C., preferably 55° C. A subsequent step of dissolving glycerin in a fraction of water in a third vessel resulting in a glycerin solution, and then dispersing carbomer into the glycerin solution, resulting in a glycerin/carbomer solution. A next step of dissolving adapalene in N-methyl-2-pyrrolidone in a fourth vessel resulting in an adapalene solution, and subsequently warming the adapalene solution to 45° C. to 65° C., preferably 55° C. A further step of adding the adapalene solution to the first homogeneous mixture under constant stirring, taking care that the difference in the temperature of the two components is not greater than 5° C., resulting in a second adapalene mixture. A further step of adding the second homogeneous mixture to the second adapalene mixture obtained strong and constant stirring, taking care that the difference in the temperature of the two components is not greater than 5° C., resulting in a third adapalene mixture. An additional step of cooling the third adapalene mixture to 35° C. to 45° C., preferably 40° C. and then adding the glycerin/carbomer solution to the cooled third adapalene mixture, resulting in a glycerin/carbomer/adapalene mixture. A final step of dissolving triethanolamine in a fraction of water resulting in a triethanolamine solution, and adding the triethanolamine solution to the glycerin/carbomer/adapalene mixture under constant stirring; and adjusting the pH to be between 4.5-5.0 by the addition of triethanolamine.

In a further embodiment, a topical composition comprises water; adapalene at a concentration of about 0.10%; N-methyl-2-pyrrolidone at a concentration of about 5.0%; oleic acid at a concentration of about 1.0%; ceteareth-12 at a concentration of about 1.5%; PEG-12 glyceryl distearate at a concentration of about 1.0%; poloxamer at a concentration of about 2.5%; butylhydroxytoluene at a concentration of about 0.1%; disodium edetate at a concentration of about 0.1%; benzyl alcohol at a concentration of about 1.0%; glycerin at a concentration of about 5.0%; carbomer at a concentration of about 1.0%; and triethanolamine at a concentration of about 0.3%.

BRIEF DESCRIPTION OF THE DRAWINGS

The above and other features, aspects, and advantages of the present invention are considered in more detail, in relation to the following description of embodiments thereof shown in the accompanying drawings, in which.

DETAILED DESCRIPTION OF THE INVENTION

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Those of ordinary skill in the art will realize that the following description of the present invention is illustrative only and not in any way limiting. Other embodiments of the invention will readily suggest themselves to such skilled persons having the benefit of this disclosure. Before describing the characteristics of the present invention, it should be understood that the descriptions of specific applications are provided only as representative examples. The present invention is not intended to be limited to the shown embodiments, but it should be given the broadest extent possible, consistent with the principles and characteristics described herein.

Definitions and Abbreviations

Both in the description and claims of the present invention, the following terminology is used according to the definitions listed below.

"Solubility" is the ability of a substance (solute) to dissolve when mixed with a liquid (solvent). Unless the text of the sentence specifically indicates something different, the referred solvent is water.

"Active principle," "active pharmaceutical ingredient," or "drug substance" is the substance responsible for the pharmacological effect of a pharmaceutical preparation. In a preferred embodiment of the present invention, the active pharmaceutical ingredient is a retinoid. In a further preferred embodiment, the retinoid is selected from the group consisting of first generation, second generation, and third generation compounds. In further embodiment, the first generation compound is selected from the group consisting of retinol, tretinoin, and isotretinoin. In another embodiment, the second generation compound is selected from the group consisting of etretinate and acitretin. In a further embodiment, the third generation compound is selected from the group consisting of tazarotene and adapalene.

"Pharmacological effect" is the observable manifestation due to a biochemical change generated by a drug substance.

"Pharmacological action" is the modification or process that starts in the presence of a drug substance. It may be a biochemical process, an enzymatic reaction, a movement of electric charges, etc. The pharmacological action causes the observable modification known as pharmacological effect.

"HLB" or "hydrophilic/lipophilic balance" is a number, on a 1 to 40 scale, that allows predicting the type of surfactant properties that a molecular structure will provide, which depends on the number and weight percentage of hydrophilic and lipophilic groups that the molecule possesses.

"Partition coefficient" or "distribution coefficient" is the ratio of concentrations of the substance in the two phases of a mixture made up of two immiscible solvents at equilibrium. Hence, the partition coefficient measures the differential solubility of a substance in two solvents. The partition coefficient formula is the following:

$$K = \frac{[\text{Substance}]_1}{[\text{Substance}]_2}$$

Where $[\text{Substance}]_1$ is the concentration of the substance in the first solvent, and $[\text{Substance}]_2$ is the concentration of the same substance in the other solvent.

"Cream, cream-gel, or lotion" are semisolid pharmaceutical preparations comprised of two immiscible phases, a continuous or external phase and a discontinuous or internal phase, in which the discontinuous or internal phase is emulsified in the form of drops or micelles in the continuous or external phase.

"Systemic absorption" or "systemic uptake" is the transition of an active pharmaceutical ingredient from the application site to the blood stream, where it is distributed throughout the body.

Figure 4:
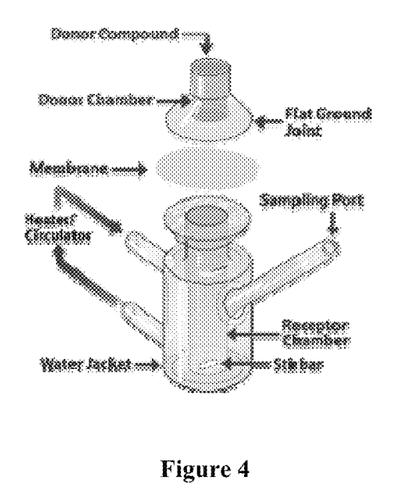
FIG. 4. Franz diffusion cell used to study the penetration of adapalene from the formulation of the present invention. (Previous state of the art)

"Franz diffusion" cells are a system used to measure the diffusion of a drug substance through a natural or synthetic membrane located between two chambers, a donor and a receiver, which are vertically assembled. Franz diffusion cells are shown in FIG. 4. These cells were used as a tool for measuring the performance of the pharmaceutical preparation of the present invention, and are not part of the invention since they are widely described in the current state of the art. The description made of the Franz diffusion cells herein is only illustrative, being its sole purpose to indicate the process used to validate the superior performance of the preparation of the present invention.

The term "about," as used herein when referring to a measurable value such as an amount of a compound, dose, time, temperature, and the like, is meant to encompass variations of 20%, 10%, 5%, 1%, 0.5%, 0.1%, 0.01% or even 0.01% of the specified amount.

DESCRIPTION

One purpose of the present invention is to provide a composition and a manufacturing method of a semisolid dosage form of a retinol preparation for topical administration, for the treatment of different diseases in which topical retinoids have proven to be useful. In one preferred embodiment, the retinoid preparation comprises an active pharmaceutical ingredient, such as adapalene. Skin conditions subject to treatment with a composition in accordance with the present invention include, but are not limited to, skin conditions with inflammatory or proliferative components, different types of acne, psoriasis, skin damage caused by the sun, among others.

More particularly, the present invention is related to a cream, cream-gel, or lotion pharmaceutical preparation whose external or continuous phase is aqueous, and where the active pharmaceutical ingredient, such as adapalene, is completely dissolved in the preparation, without evidence, at the microscopic level, about the presence of crystals of the active pharmaceutical ingredient.

The preparation of the present invention is achieved by solubilizing the active pharmaceutical ingredient in a pharmaceutically acceptable solvent, capable of dissolving at least 3 mg/mL of adapalene at room temperature. Preferably, the solvent should be capable of dissolving at least 100 mg/mL of adapalene at room temperature. Afterwards, the solution of the active pharmaceutical ingredient is incorporated into the aqueous preparation, together with a carefully selected lipid which produces a mixture with a partition coefficient of between 0.95 and 1 for the active ingredient, preferably adapalene.

The lipid-solvent mixture, when incorporated in a cream, cream-gel, or lotion aqueous vehicle, prevents the active pharmaceutical ingredient from being partition into the water/aqueous phase in the vehicle, thereby avoiding recrystallization of the active pharmaceutical ingredient, such as adapalene, and keeping it in solution in the preparation.

Figure 5:
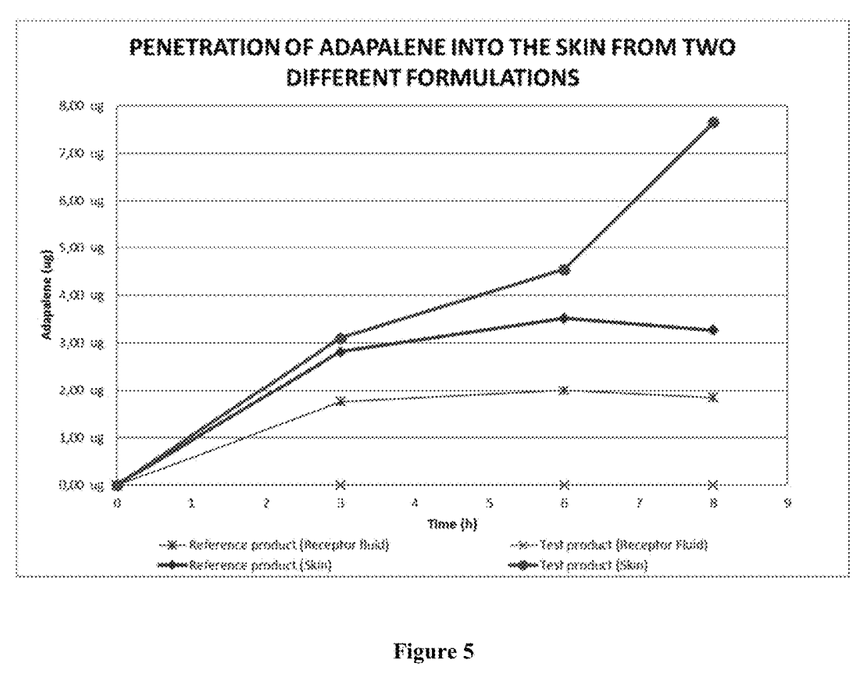
FIG. 5. Results of the penetration study of adapalene into the skin in Franz diffusion cells, using pig skin as membrane. A comparative study between the pharmaceutical preparation of the present invention (test preparation) and the conventional preparation in which adapalene is dispersed, undissolved, in an aqueous gel (reference preparation).

Because of the soluble state in which adapalene is incorporated into the pharmaceutical preparation of the present invention, both the amount of and the speed with which the active pharmaceutical ingredient penetrates through the skin are significantly increased. This effect is illustrated in FIG. 5, which shows that the amount of adapalene penetrating through pig skin, in a Franz diffusion cell model, is higher with the use of the preparation of the present invention, compared to the use of a traditional preparation in which adapalene is simply suspended or dispersed in an aqueous vehicle.

The topical pharmaceutical preparations of active pharmaceutical ingredient, such as adapalene, made primarily in aqueous vehicles, which do not generate an oily, unpleasant sensation when applied to the skin, but at the same time, containing adapalene in soluble form rather than merely dispersed or suspended, maximizing penetration through the different layers of the skin.

A pharmaceutical vehicle that allows the dissolution of the active pharmaceutical ingredient in the minimum possible amount of a non-aqueous solvent system is provided herein. The vehicle must have very specific characteristics in terms of HLB (hydrophilic/lipophilic balance) and partition coefficient in water, so as to enable its incorporation by emulsification in an aqueous external or continuous phase, without promoting the recrystallization of the active pharmaceutical ingredient, such as adapalene, in the vehicle.

The present invention comprises pharmaceutical compositions and manufacturing methods of topical adapalene preparations to treat skin diseases. An example of the formulation is shown in Table 1.

TABLE 1

Example of the formulation

| MATERIAL | % | FUNCTION |
|---|---|---|
| Adapalene | 0.1% | Active pharmaceutical ingredient |
| N-methyl-2-pirrolidone (Pharmasolve) | 5.0% | Solvent |
| Oleic acid | 1.0% | Lipid |
| Ceteareth-12 (Eumulgin B1) | 1.5% | Surfactant |
| PEG-12 Glyceryl distearate | 1.0% | Surfactant |
| Poloxamer (Lutrol F68) | 2.5% | Surfactant |
| Butylhydroxytoluene | 0.1% | Antioxidant |
| Disodium edetate | 0.1% | Chelating agent |
| Benzyl alcohol | 1.0% | Preservative |
| Glycerin | 5.0% | Humectant |
| Carbomer (Carbopol 971P) | 1.0% | Gelling agent |
| Triethanolamine | 0.3% | Ph modifier |
| Purified water | 81.4% | Vehicle |
| Total | 100.0% | |

In Table 1, the concentrations of all components are expressed as weight/weight (w/w) percentage. The same unit is used throughout this document, unless something else is specifically stated.

Adapalene is the active pharmaceutical ingredient and the main component of the exemplary formulation. In prior art formulations, this active pharmaceutical ingredient is contained in formulations from 0.02% to 0.3%. However, because the formulation of the invention makes the active pharmaceutical ingredient more effective, the effective dose range is between about 0.05% to 0.2%. Preferably, formulations comprise between about 0.05% to 0.10% of active pharmaceutical ingredient, such as adapalene.

Another primary aspect of the invention is to provide a lipid-solvent complex, which presents a partition coefficient for the active pharmaceutical ingredient, such as adapalene, to water of 0.95 to 1. One of the functions of the complex is to maintain the active pharmaceutical ingredient dissolved, even when the mixture is incorporated into a vehicle with high water content. The physicochemical properties of the solvent-lipid complex prevent adapalene from doing partition with water in the preparation, thus avoiding recrystallization of the active pharmaceutical ingredient. Another function of the solvent-lipid complex is to improve penetration of the active pharmaceutical ingredient into the skin and create a depot effect in the epidermis and dermis, increasing the amount of the active pharmaceutical ingredient in the action site.

In one preferred embodiment, the solvent is N-methyl-2-pyrrolidone (Pharmasolve®, ISP Investments Inc.) is used to solubilize the active pharmaceutical ingredient, prior to combining it with the lipid. It is used at a concentration in the range of about 1.0% to 15%, and more preferably at a concentration in the range of about 2.0% to 8.0%. Other solvents may include diethylene glycol monoethyl ether (Transcutol®, Gattefosse S.A.S.), 2-pyrrolidone, glycofurol, and dimethyl sulfoxide.

In one preferred embodiment, the lipid used is oleic acid. When mixed with the solution of the active pharmaceutical ingredient in the solvent, oleic acid provides the partition coefficient and HLB necessary to maintain it in solution, and thus provides the desired effects of improved absorption and the depot effect into the skin. In one preferred embodiment, the partition coefficient is between 0.95 and 1.0 and an HLB of between 1.0 to 1.5. It is included at a concentration in the range of about 0.5% to 10%. Other acceptable lipids include stearic acid, linoleic acid, ethyl linoleate, and methyl linoleate.

In addition to the three components described above, the preferred formulation includes other ingredients that increase the effectiveness and provide other advantages to the composition. These ingredients are described below.

Ceteareth-12 (Eumulgin® B1, Cognis IP Management GMBH) functions as an emulsifying agent located in the oil phase, providing physical stability to the cream or lotion. It may be included at a concentration in the range of about 0.5% to 5.0%. Equivalent components include any product from the series of polyethoxylated alkyl ethers, any product from the series of polyethoxylated castor oil derivatives, and any product from the series of diacylglycerol-polyethylene glycol conjugates, especially PEG-12 glyceryl distearate, PEG-12 glyceryl dimyristate, PEG-23 glyceryl distearate, or mixtures thereof.

Poloxamer 188 (Lutrol® F68, BASF Aktiengesellschaft) also functions as an emulsifying agent, providing physical stability to the cream or lotion. Unlike ceteareth 20, poloxamer 188 is located in the aqueous phase. It is included at a concentration in the range of about 0.5% to 10%. Equivalent components include any product from the series of polyethoxylated sorbitan fatty acid esters, and any product from the series of sorbitan esters (sorbitan fatty acid esters), or mixtures thereof.

Butylhydroxytoluene is included as antioxidant in order to avoid the oxidation of the active pharmaceutical ingredient. Butylhydroxytoluene is included at a concentration in the range of about 0.0075% to 0.5%. The composition may include other equivalent antioxidants. Alternative antioxidants include butylhydroxyanisole at a concentration in the range of about 0.005% to 0.5%, alpha-tocopherol at a concentration in the range of about 0.001% to 0.1%, ascorbyl palmitate at a concentration in the range of about 0.025% to 0.1%, propyl gallate at a concentration in the range of about 0.002% to 0.2%, or mixtures thereof.

Disodium edetate, a chelating agent, is part of the antioxidant system to avoid oxidation of the active pharmaceutical ingredient. It is also important in order to stabilize the carbomer gel. Disodium edetate is included at a concentration in the range of about 0.005% to 0.2%. Equivalent components include citric acid at a concentration in the range of about 0.1% to 3.0%, EDTA at a concentration in the range of about 0.005% to 0.2%, fumaric acid at a concentration in the range of about 0.1% to 3.0%, and malic acid at a concentration in the range of about 0.1% to 3.0%.

Benzyl alcohol may be included as a preservative to deter microbial contamination, at a concentration in the range of about 0.5% to 5.0%. Equivalent preservatives include benzoic acid at a concentration in the range of about 0.01% to 0.3%, boric acid at a concentration in the range of about 0.1% to 2.0%, butylparaben at a concentration in the range of about 0.05% to 0.5%, cetrimide at a concentration in the range of about 0.005% to 3.0%, chlorocresol at a concentration in the range of about 0.05% to 0.3%, methylparaben at a concentration in the range of about 0.05% to 0.5%, propylparaben at a concentration in the range of about 0.01% to 0.5%, phenoxyethanol at a concentration in the range of about 0.1% to 2.0%, phenylethyl alcohol at a concentration in the range of about 0.1% to 2.0%, sodium or potassium benzoate at a concentration in the range of about 0.05% to 2.0%, potassium sorbate at a concentration in the range of about 0.05% to 1.0%, or mixtures thereof.

Glycerin is included as a humectant, and to decrease the irritation caused by the active pharmaceutical ingredient. Concentrations ranging from approximately 1.0% to 15% can be used. Equivalent components include propylene glycol, polyethylene glycol, and sorbitol. Carbomer functions as a viscosity-increasing agent, and also as an emulsifying agent. It provides enhanced physical stability and improves the organoleptic properties of the cream or lotion. It is included at a concentration in the range of about 0.3% to 3.0%. Equivalent components include any product of the series of carbomers, polycarbophil, hydroxypropyl methylcellulose, methylcellulose, and carboxymethyl cellulose.

Triethanolamine is used as an alkalizing agent, thereby increasing the viscosity of the carbomer gel. It also modifies the pH of the cream to a pH value suitable for topical use. It is used at a concentration in the range of about 0.1% to 2.0%. Equivalent components include diethanolamine, monoethanolamine, triethylamine, sodium hydroxide, and potassium hydroxide.

Water is the major component of the preparation and is especially important for the performance of the formula, because it provides the vehicle that sustains all other ingredients. Water makes up the external or continuous phase of the emulsion, giving the preparation a non-greasy sensation at the time of application. It is used at a concentration in the range of about 70% to 90%.

The preferred formulation is a white cream-gel. Its texture and consistency are smooth, uniform and non-greasy. Its viscosity can be adjusted to be applied either in the form of cream-gel packaged in a collapsible tube, or as a lotion to be atomized on the skin. When it's microscopically analyzed, no crystals of the active pharmaceutical ingredient are observed. Without being bound to a theory, it is believed that the composition is a cream-gel whose external phase is an aqueous gel, whereas the internal phase is composed of micelles, mostly nanometric, formed by the solution of the active pharmaceutical ingredient in the solvent-lipid complex. Due to the partition coefficient of the active pharmaceutical ingredient between the solvent-lipid complex and the aqueous external phase, the active pharmaceutical ingredient tends to stay within the micelle and is slowly released over the time. Surprisingly, this results in a depot effect, which provides for the active pharmaceutical ingredient to be released and metabolized locally and, therefore, the absorption into the bloodstream is reduced. A direct consequence of that is that a higher amount of the active pharmaceutical ingredient remains in the outer layers of the skin, without increasing the amount of the active pharmaceutical ingredient in the deeper layers (for example, hypodermis), which are highly vascularized. Accordingly, the systemic absorption and systemic adverse effects of the active pharmaceutical ingredient are reduced.

This advantage is achieved by a combination of two effects: first, the active pharmaceutical ingredient is dissolved before being incorporated into the formulation; and second, the partition coefficient for the active pharmaceutical ingredient between the solvent-lipid complex and the aqueous external phase is greater than 0.95. If the active pharmaceutical ingredient is dissolved only in a solvent without the formation of the solvent-lipid complex to provide the required partition coefficient, the active pharmaceutical ingredient would recrystallize when being added to the aqueous external phase, losing all comparative advantages over the formulations described in the state of the art.

The experiment described in Example 2 demonstrates the reduction in systemic absorption. The amount of the active pharmaceutical ingredient in the medium of the receiver chamber is an indirect measure of the amount thereof, which is capable of reaching the systemic circulation. The study shows that the amount of the active pharmaceutical ingredient in the medium of the receiver chamber is significantly decreased due to the characteristics of the preparation of the present invention.

In one aspect, the invention is a composition for treating different skin conditions by topical administration. The composition comprises water, adapalene at a concentration in the range of about 0.05% to 0.1%, and a complex consisting of a solvent and a lipid with a partition coefficient value of adapalene in the aqueous external phase of 0.95 to 1. The solvent is preferably selected from the group comprising N-methyl-2-pyrrolidone (Pharmasolve), diethylene glycol monoethyl ether (Transcutol), 2-pyrrolidone, glycofurol, and dimethylsulfoxide, used at a concentration in the range of about 1.0% to 15%, and more preferably in the range of about 2.0% to 8.0%. The lipid is preferably selected from the group comprising oleic acid, stearic acid, linoleic acid, ethyl linoleate, and methyl linoleate, used at a concentration in the range of about 0.5% to 10%. The composition may further comprise one or more surfactants. The composition may further comprise one or more antioxidants. The composition may further comprise one or more chelating agents. The composition may further comprise one or more preservatives. The composition may further comprise one or more humectants. The composition may further comprise one or more gelling agents. The composition may further comprise one or more pH modifiers.

In another aspect, the invention is a method of manufacturing a composition comprising the steps described in Example 1.

In another aspect, the invention is a composition for treating different skin conditions by topical administration, wherein the composition is comprised of: water; adapalene at a concentration of about 0.1%; N-methyl-2-pyrrolidone (Pharmasolve) at a concentration of about 5.0%; oleic acid at a concentration of about 1.0%; ceteareth-12 (Eumulgin B1) at a concentration of about 1.5%; PEG-12 glyceryl distearate at a concentration of about 1.0%; poloxamer (Lutrol F68) at a concentration of about 2.5%; butylhydroxytoluene at a concentration of about 0.1%; edetate disodium at a concentration of about 0.1%; benzyl alcohol at a concentration of about 1.0%; glycerin at a concentration of about 5.0%; carbomer (Carbopol® 971P, B. F. Goodrich Company) at a concentration of about 1.0%; and triethanolamine at a concentration of about 0.3%. According to such an embodiment, the composition is applied to the patient's skin to treat the affected area.

In yet a further embodiment of the present invention, a method for preparing the topical composition is provided, which comprises the following steps. A first step of combining ceteareth-12, oleic acid and PEG-12 glyceryl distearate are combined and warming the mixture to 45° C. to 65° C., preferably 55° C., under constant stirring, until obtaining a first homogeneous mixture; dissolving butylhydroxytoluene into the first homogeneous mixture. An additional step of dissolving disodium edetate, benzyl alcohol and poloxamer in a second vessel, in a fraction of water resulting in a second homogeneous mixture, and subsequently warming the second homogeneous mixture to 45° C. to 65° C., preferably 55° C. A subsequent step of dissolving glycerin in a fraction of water in a third vessel resulting in a glycerin solution, and then dispersing carbomer into the glycerin solution, resulting in a glycerin/carbomer solution. A next step of dissolving adapalene in N-methyl-2-pyrrolidone in a fourth vessel resulting in an adapalene solution, and subsequently warming the adapalene solution to 45° C. to 65° C., preferably 55° C. A further step of adding the adapalene solution to the first homogeneous mixture under constant stirring, taking care that the difference in the temperature of the two components is not greater than 5° C., resulting in a second adapalene mixture. A further step of adding the second homogeneous mixture to the second adapalene mixture obtained strong and constant stirring, taking care that the difference in the temperature of the two components is not greater than 5° C., resulting in a third adapalene mixture. An additional step of cooling the third adapalene mixture to 35° C. to 45° C., preferably 40° C. and then adding the glycerin/carbomer solution to the cooled third adapalene mixture, resulting in a glycerin/carbomer/adapalene mixture. An final step of dissolving triethanolamine in a fraction of water resulting in a triethanolamine solution, and adding the triethanolamine solution to the glycerin/carbomer/adapalene mixture under constant stirring; and adjusting the pH to be between 4.5-5.0 by the addition of triethanolamine.

EXAMPLES

Example 1: Preparation of the Adapalene Formulation

A sample of 200 g of cream was prepared.
The preferred formulation as described in Table 1 was prepared as follows:

Step 1. Ceteareth-12 (Eumulgin B1), oleic acid and PEG-12 glyceryl distearate were combined and warmed to 55° C. under constant stirring, until obtaining a homogeneous mixture.

Step 2. Butylhydroxytoluene was dissolved into the mixture obtained in Step 1.

Step 3. In a second vessel, disodium edetate, benzyl alcohol and poloxamer were dissolved in a fraction of water, and subsequently the mixture was warmed to 55° C.

Step 4. In a third vessel, glycerin was dissolved in a fraction of water, and then carbomer was dispersed into the solution.

Step 5. In a fourth vessel, adapalene was dissolved in N-methyl-2-pyrrolidone (Pharmasolve), and subsequently the solution was warmed to 55° C. The adapalene solution was added to the mixture obtained in Step 2 under constant stirring, taking care of keeping the temperature at 55° C.±3° C.

Step 6. The mixture obtained in Step 3 was added to the mixture obtained in Step 5 under strong and constant stirring, taking care of keeping the temperature at 55° C.±3° C.

Step 7. The mixture obtained in Step 6 was cooled to 40° C.

Step 8. The mixture obtained in Step 4 was added to the mixture obtained in Step 7 under strong and constant stirring.

Step 9. Triethanolamine was dissolved in a fraction of water, and this solution added to the mixture obtained in Step 8 under constant stirring.

Step 10. pH was tested to be between 4.5-5.0.

Example 2: Diffusion Study Using the Franz Diffusion Cells

A study was performed to assess the effect obtained with the use of the present invention in terms of adapalene transdermal penetration, compared to a conventional or reference formulation.

A reference formula sample of 200 g was manufactured, containing the same ingredients and the same proportions as those used in the preferred formulation of the present invention included in Table 1, except for the components that make up the solvent-lipid complex, which were eliminated. In this way, the active pharmaceutical ingredient is not kept in solution but, on the contrary, is dispersed as finely divided particles in the preparation. The manufacturing process used was similar to that described in Example 1. The reference formulation used in the study is described below in Table 2.

TABLE 2

Reference formulation

| MATERIAL | % | FUNCTION |
| --- | --- | --- |
| Adapalene | 0.1% | Active pharmaceutical ingredient |
| Ceteareth-12 (Eumulgin B1) | 1.5% | Surfactant |
| PEG-12 Glyceryl distearate | 1.0% | Surfactant |
| Poloxamer (Lutrol F68) | 2.5% | Surfactant |
| Butylhydroxytoluene | 0.1% | Antioxidant |
| Disodium edetate | 0.1% | Chelating agent |
| Benzyl alcohol | 1.0% | Preservative |
| Glycerin | 5.0% | Humectant |
| Carbomer (Carbopol 971P) | 1.0% | Gelling agent |
| Triethanolamine | 0.3% | Ph modifier |
| Purified water | 87.4% | Vehicle |
| Total | 100.0% | |

Six standard Franz diffusion cells (FIG. 4) were used. The dimensions were identical for all of the 6 cells. The donor chamber had a nominal volume of 1 mL, whereas the receiver chamber had a nominal volume of 5 mL. The actual diffusion area was 0.636 cm$^2$. Both stirring and temperature of the cells were monitored throughout the experiment and were kept identical for all of the 6 cells.

The ears were stored at freezing temperature (−10° C. to −15° C.) since the time of slaughter. Twenty-four hours before the test, the ears were removed from the freezer and thawed to room temperature. Once thawed, they were cleaned with drinking water and dried with an absorbent towel. The layer of skin consisting of stratum corneum, epidermis and dermis was separated from the other layers using a scalpel. The remaining fat and blood vessels were removed to get six sheets of skin of the same thickness, about 2 mm.

The skin sheets were hydrated for 12 hours in phosphate buffer at a pH 7.4, at cooling temperature (2° C. to 8° C.). Then they were mounted over the cell containing the receptor medium, making sure that no bubbles were present in the medium-membrane interface. Normal saline solution containing 0.2% polysorbate 80 was used as receptor medium. The experiment was carried out with six cells for both products: the conventional or reference formulation and the test formulation. For each formulation, 2 samples were taken at 3 hours, 2 samples at 6 hours and finally two samples at 8 hours. The experiment was conducted twice for each formulation in order to obtain four inputs/data at each one of the sampling times. At each sampling time, 2 cells were removed for each product, and both the skin sample and the receptor medium were taken. Samples were analyzed using a validated HPLC methodology. In the case of the receptor medium, a sample was directly injected into the equipment. In the case of the skin samples, they were removed and their exterior face washed, in order to eliminate any trace of adapalene adhered to the surface. The samples were then dried with an absorbent towel, cut into 8 smaller pieces, and the extraction performed with 2 mL of acetonitrile for 45 minutes under sonicating conditions.

The curves resulting from average data of each of the formulations, for both the sample of the receptor medium and the sample of the skin, are plotted in FIG. 5.

The amount of adapalene accumulated in the layers of the skin (stratum corneum, epidermis and dermis) was significantly higher at each one of the assessment times for the test formulation in comparison to the reference or conventional formulation.

The amount of adapalene reaching the receptor medium was significantly lower for the test formulation compared to the reference or conventional formulation, in each of the sampling times evaluated.

This result combined with the result obtained in the skin, leads to the conclusion that the increase in the amount of adapalene that penetrates the skin with the test formulation does not imply an increase in the amount of adapalene reaching the receptor medium.

The results of this study suggest that is possible to obtain higher delivery of adapalene at the site of action when the test formulation of the present invention is used, without implying a higher systemic absorption and, therefore, increased adverse effects.

Figure 1:
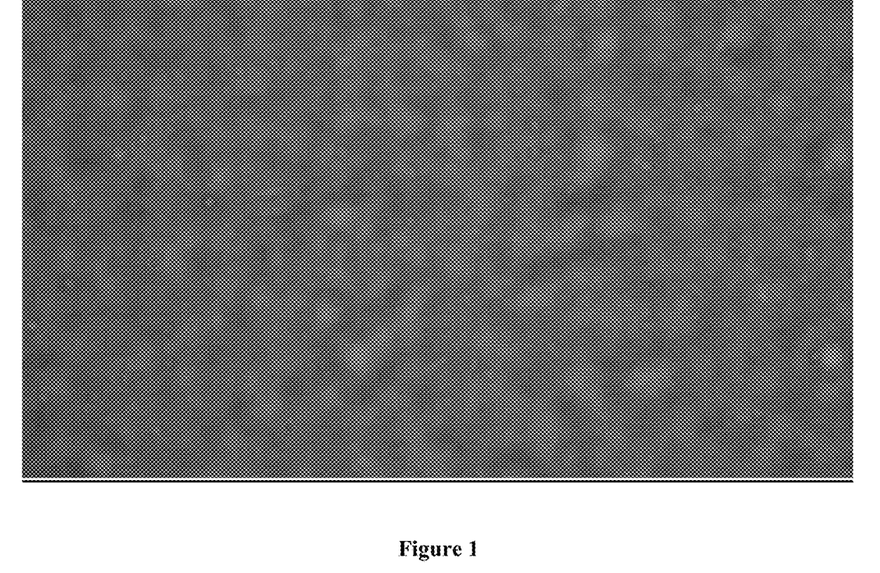
FIG. 1. Photomicrograph of the pharmaceutical preparation of the present invention, taken on inverted microscope using a 100× objective.

Turning to FIG. 1, a photomicrograph of the pharmaceutical preparation of the present invention, taken on inverted microscope using a 100× objective is shown. In the picture, it is evident that there is no presence of crystals of adapalene in the preparation. Other solid structures are not observed either; on the contrary, only completely spherical structures are observed, which suggests the exclusive presence of micelles containing non-aqueous internal phase, and dispersed in the aqueous external phase. These micelles of non-aqueous components, as well as other nanometer-sized particles which are not detectable by optical microscopy, contain the active pharmaceutical ingredient in soluble state.

Figure 2:
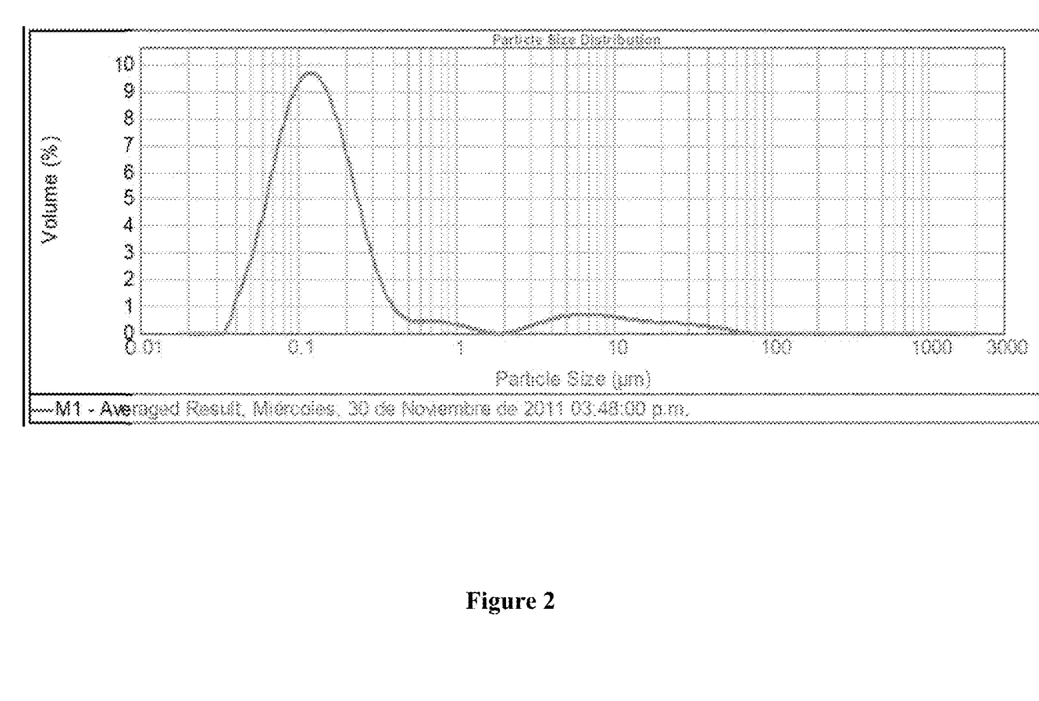
FIG. 2. Particle (drop) size of the pharmaceutical preparation of the present invention, measured by the laser diffraction method with Mastersizer 2000, from Malvern Instruments Ltd.

Then, in FIG. 2 the particle size distribution of the pharmaceutical preparation of the present invention, measured by the laser diffraction method using the Mastersizer 2000 equipment, from Malvern Instruments Ltd is provided. The report indicates that most of the particles present in the preparation, more than 90% of the total, are at nanoscale. These particles have an average size of 119 nm, which is why the presence of solid particles is discarded. The nanometric particles detected by the equipment correspond to micelles of the non-aqueous internal phase emulsified in the aqueous external phase. A small population of particles is also observed, corresponding to less than 10% of the total, whose average size is close to 7 micrometers. These particles are micelles visible with optical microscope, and are described in FIG. 1.

Figure 3:
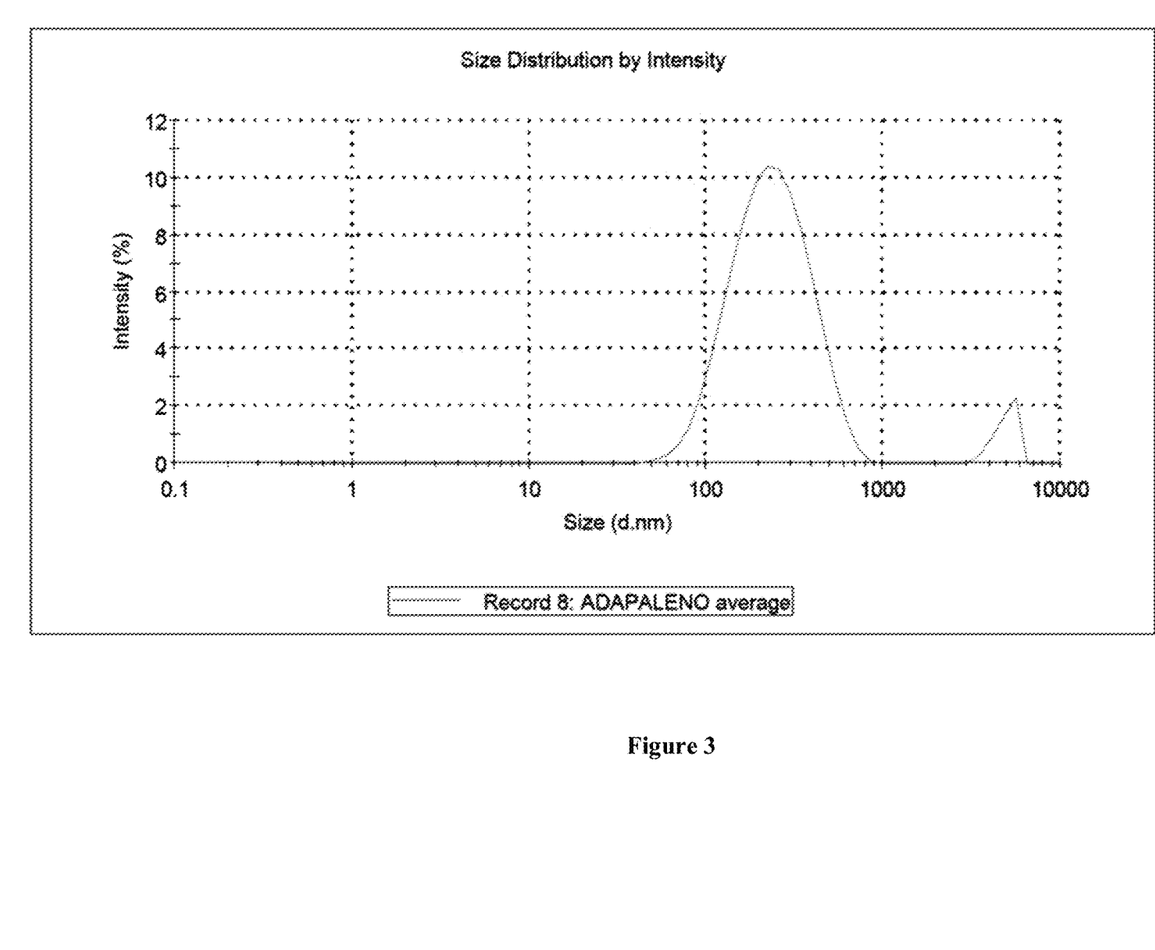
FIG. 3. Particle (drop) size of the pharmaceutical preparation of the present invention, measured by Z potential method with Zetasizer, from Malvern Instruments Ltd.

In FIG. 3, the particle size distribution of the pharmaceutical preparation of the present invention, measured by the Z potential method using the Zetasizer equipment, from Malvern Instruments Ltd. The report confirms that the population of particles in the preparation are at nanoscale, presenting an average size of 194 nm. These results confirm the measurements made by the laser diffraction method shown in FIG. 2.

Using both methods as shown in FIGS. 2 and 3, it was determined that most of the particles present in the preparation, more than 90%, are at nanoscale, between 100 and 200 nanometers, and correspond to the expected size of the drops or micelles of the non-aqueous internal phase, which is emulsified into the external aqueous phase. There are no bigger solid particles or crystals detected in the samples.

In FIG. 4 the assembly of the Franz diffusion cells, which were used for the comparative performance tests of the preparations in terms of penetration into the skin are shown. These cells were used as a tool and are not part of the invention since they are widely described in the current state of the art. The description made of the Franz diffusion cells herein is only illustrative, being its sole purpose to indicate the process used to validate the superior performance of the preparation of the present invention.

A quantity of each preparation was accurately weighed and placed in the donor chamber. The system was assembled using 4 cm$^2$ of pig ear skin of uniform thickness, previously treated, as the membrane. The receiver chamber was filled with physiological medium. The system was stabilized at 37° C. by recirculating water from a thermostated bath through a heating jacket. Samples were taken from the receiver chamber and the pig skin acting as membrane, at each time defined in the protocol. Samples were analyzed by HPLC using a validated analytical method. The same assembly was repeated enough times to get duplicate points at each of the selected sampling times and for each of the tested preparations.

Finally, FIG. 5 shows the comparative results of the penetration test of adapalene from the two preparations. The test preparation, corresponding to the present invention, is a formulation in which adapalene is dissolved in a solvent-lipid complex, which in turn is emulsified in an aqueous gel. The reference preparation corresponds to a gel prepared according to the current state of the art, in which micronized adapalene having an average particle size <30 μm, is suspended, undissolved, in an aqueous gel.

The curve labeled "Skin" corresponds to the amount of adapalene extracted from pig skin, which acted as membrane, at each of the sampling times. The curve labeled "Medium" corresponds to the amount of adapalene found in the physiological medium located in the receiver chamber, at each of the sampling times.

FIG. 5 shows that the amount of adapalene penetrating into the skin is higher with the preparation of the present invention in comparison with the use of the reference preparation. This phenomenon is observed at all sampling times. It is also observed that the amount of adapalene that reaches the receiver fluid is lower with the preparation of the present invention in comparison with the use of the reference preparation. When the test preparation was used, the amount of adapalene in the receiver fluid was below the quantification limit of the analytical method at all sampling times.

In conclusion, FIG. 5 shows that the use of the preparation of the present invention achieves higher levels of adapalene into the skin, while the amount of the active pharmaceutical ingredient that passes through the skin and becomes available to achieve the blood stream is reduced.

FIG. 5 also shows that the amount of adapalene able to pass through the skin and reach the receiver fluid is less using the pharmaceutical preparation of the present invention, compared to the use of a traditional preparation of adapalene. This phenomenon is due to the formation of a depot, or excess, of the active pharmaceutical ingredient into the skin, facilitated by the solvent-lipid complex that keeps adapalene in a solution. This phenomenon, referred to herein as the "depot effect" is desirable from a therapeutic point of view, because it is there where the active pharmaceutical ingredient exerts its pharmacological action. In addition, this depot decreases the amount of adapalene that reaches the general circulation, which is directly related to the occurrence of undesirable side effects. The "depot effect" means that the active pharmaceutical ingredient is released and metabolized locally and, therefore, the absorption into the blood stream is reduced.

Although the embodiments and applications of the present invention have been shown and described, it would be evident to those skilled in the art and knowing this description that many more different modifications from those mentioned above are possible without departing from the inventive concepts of this document. Therefore, the invention should be restricted only to the spirit of the claims.

What is claimed is:

1. A topical composition, comprising:
   water;
   adapalene at a concentration in a range of about 0.05% to 0.1%; and
   a complex consisting of a solvent selected from the group consisting of N-methyl-2-pyrrolidone, diethylene glycol monoethyl ether, 2-pyrrolidone, glycofurol, or mixtures thereof, and a lipid selected from the group consisting of oleic acid, stearic acid, linoleic acid, ethyl linoleate, methyl linoleate, or mixtures thereof, which dissolve the adapalene and has a partition coefficient value for adapalene in water of 0.95 to 1.

2. The composition of claim 1, wherein the solvent is present at a concentration in a range of about 1.0% to 15%.

3. The composition of claim 1, wherein the lipid is present at a concentration in a range of about 0.5% to 10%.

4. The composition of claim 1, further containing one or more surfactants, one or more antioxidants, one or more chelating agents, one or more preservatives, one or more humectants, one or more gelling agents, and one or more pH modifiers.

5. The composition of claim 4, wherein the antioxidant is selected from the group consisting of butylhydroxytoluene, butylhydroxyanisole, alpha-tocopherol, propyl-gallate, and mixtures thereof.

6. The composition of claim 4, wherein the chelating agent is selected from the group consisting of disodium edetate, citric acid, EDTA, fumaric acid, and malic acid.

7. The composition of claim 4, wherein the preservative is selected from the group consisting of benzyl alcohol, benzoic acid, boric acid, butylparaben, cetrimide, chlorocresol, methylparaben, propylparaben, phenoxyethanol, phenylethyl alcohol, sodium benzoate, potassium benzoate, potassium sorbate, and mixtures thereof.

8. The composition of claim 4, wherein the humectant is selected from the group consisting of glycerin, propylene glycol, polyethylene glycol, and sorbitol.

9. The composition of claim 1 prepared as cream-gel, in which the external or continuous phase is hydrophilic and the internal or discontinuous phase is lipophilic.

10. The composition of claim 1 which, when tested under de microscope, does not show crystals of the active pharmaceutical ingredient.

11. The composition of claim 1, further comprising an emulsifying agent.

12. The composition of claim 11, wherein the emulsifying agent is selected from the group consisting of ceteareth 12, a polyethoxylated alkyl ether, polyexthoxylated castor oil derivatives, a diacylglycerol-polyethylene glycol conjugate, a poloxamer 18, carbomer.

13. The composition of claim 12, wherein the diacylglycerol-polyethyline glycol conjugate is selected from the group consisting of PEG 12 glyceryl distearate, PEG 12 glyceryl dimyristate, PEG 23 glyceryl distearate, or mixtures thereof.

14. The composition of claim 1, further comprising a viscosity-increasing agent selected from the group consisting of a carbomer, polycarbophil, hydroxypropylmethylcellulose, methylcellulose, and carboxymethyl cellulose.

15. The composition of claim 1, further comprising an alkalizing agent selected from the group consisting of triethanolamine, diethanolamine, monoethanolamine, thriethylamine, sodium hydroxide, and potassium hydroxide.

16. A topical composition, comprising:
   water;
   adapalene at a concentration of about 0.10%;
   N-methyl-2-pyrrolidone at a concentration of about 5.0%;
   oleic acid at a concentration of about 1.0%;
   ceteareth-12 at a concentration of about 1.5%;
   PEG-12 glyceryl distearate at a concentration of about 1.0%;
   poloxamer at a concentration of about 2.5%;
   butylhydroxytoluene at a concentration of about 0.1%;
   disodium edetate at a concentration of about 0.1%;
   benzyl alcohol at a concentration of about 1.0%;
   glycerin at a concentration of about 5.0%;
   carbomer at a concentration of about 1.0%; and
   triethanolamine at a concentration of about 0.3%.

* * * * *